US00PP29575P2

(12) United States Plant Patent
Brand

(10) Patent No.: US PP29,575 P2
(45) Date of Patent: Aug. 7, 2018

(54) ***PRUNUS* X *CISTENA* 'UCONNPC001'**

(50) Latin Name: *Prunus x cistena*
Varietal Denomination: UCONNPC001

(71) Applicant: University of Connecticut, Farmington, CT (US)

(72) Inventor: Mark Brand, Farmington, CT (US)

(73) Assignee: University of Connecticut, Office of the Vice President for Research, Farmington, CT (US)

( * ) Notice: Subject to any disclaimer, the term of this patent is extended or adjusted under 35 U.S.C. 154(b) by 0 days.

(21) Appl. No.: 15/731,338

(22) Filed: May 30, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP5,003 P 3/1983 Schmidt, III

*Primary Examiner* — Annette H Para
(74) *Attorney, Agent, or Firm* — Michael Best & Friedrich LLP

(57) ABSTRACT

This invention relates to a compact, purple-leaf sand cherry plant that is easy to product, exhibits reliable landscape performance and colorful ornamental traits as shown herein and described.

7 Drawing Sheets

STATEMENT REGARDING FEDERALLY SPONSORED RESEARCH OR DEVELOPMENT

Figure 1:
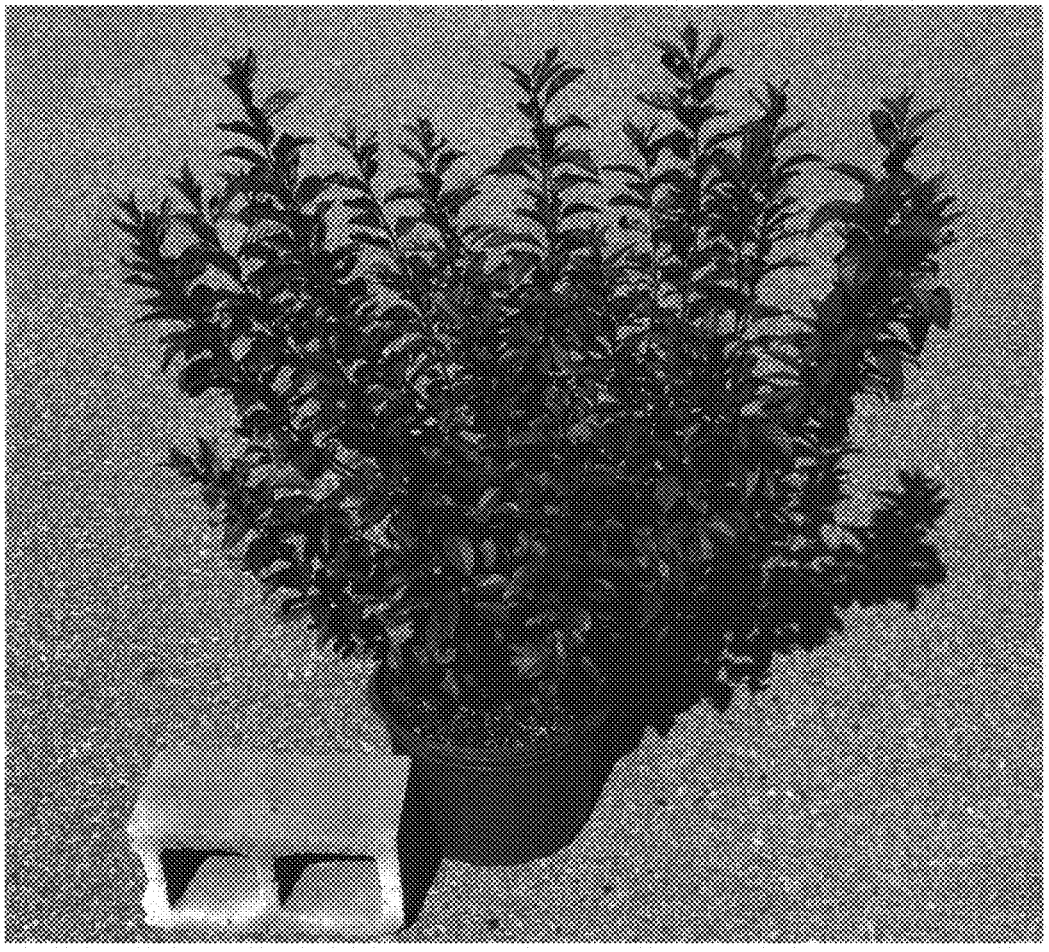

This invention was made with government support under grant 2015-31200-06009 awarded by the USDA. The government has certain rights in the invention.

BACKGROUND OF THE INVENTION

The present invention relates to a new and distinct cultivar of Sand Cherry plant, botanically known as *Prunus* x *cistena* and hereinafter referred to by the name 'UCONNPC001'.

The new Sand Cherry plant is a product of a planned breeding program conducted by the inventor in Storrs, Conn. The new Sand Cherry plant originated from a cross-pollination conducted by the Inventor during the spring of 2012 of Sand Cherry hybrid (*Prunus pumila* var. *depressa* x *Prunus pumila* var. *susquehanae*) not patented, as the female, or seed parent and Purple-leaf Cherry Plum *Prunus cerasifera* var. *atropurpurea*, not patented, as the male, or pollen, parent. The new Sand Cherry plant was discovered and selected by the Inventor during the spring of 2016 as a single plant from within the progeny of the stated cross-pollination in a controlled environment in Storrs, Conn.

Asexual reproduction of the new Sand Cherry plant by softwood stem cuttings and in vitro micropropagation in a controlled greenhouse or laboratory environment in Storrs, Conn. since June of 2014 has shown that the unique features of this new Sand Cherry plant are stable and reproduced true to type in successive generations of asexual reproduction.

SUMMARY OF THE INVENTION

Plants of the new Sand Cherry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of the new Sand Cherry plant: Grows to 4' to 5' tall with a similar spread. Plants are densely branched with branching occurring low to the ground. The result is an upright growing, but full, dense and rounded outline. Flowering is profuse in April, with the production of numerous small (1.5 to 2 cm diameter), single, 5-petaled, pink, slightly fragrant flowers. Flowers attract pollinators. Fruits are scarce due to the hybrid nature of the plant, but when present are black-purple and about 1 cm in diameter. Spring and early summer foliage is a vivid reddish purple which becomes more muted as the summer progresses. Leaves in shade may become purplish-dark green. Leaves are typically between 5 and 8 cm long and 3 to 4 cm wide with acute bases and tips. Leaf margins are serrate. Propagation is easy by rooting of firm softwood cuttings and by micropropagation. Plants are easy to grow in containers using standard container nursery production practices. Cold hardiness has not been fully evaluated, but the plant should be fully hardy as far north as zone 3. Plants are well-adapted to a variety of challenging landscape uses. These characteristics in combination distinguish 'UCONNPC001' as a new and distinct Sand Cherry plant:

1. Rounded or mounded habit;
2. Dense branching even at base of plant;
3. Mature size of 140 cm tall by 180 cm wide;
4. Heavy flowering (Meaning that flowers occur on nearly all branches, with flower clusters present at each node from the branch tip to close to the branch base. In bloom, branches appear as solid columns or wands of flowers—See FIGS. 6 and 7);
5. Red-purple spring and summer foliage; and
6. Easy propagation and culture.

Plants of the new Sand Cherry can be compared to plants of the first created *Prunus* x *cistena*, purple-leaf sand cherry. The original *Prunus* x *cistena* was created in 1910 by N. E. Hansen at South Dakota State University. This hybrid was the result of a cross between *Prunus pumila* var. *besseyi* and *Prunus cerasifera* var. *purpurea*. Plants of the new Sand Cherry differ primarily from plants of the original *Prunus* x *cistena* in their size, habit and form. *Prunus* x *cistena* grows to a mature height of 7' to 10' tall and a 6' to 8' wide, while *Prunus* x *cistena* 'UCONNPC001' grows 4' to 5' tall and 5' to 6' wide. *Prunus* x *cistena* has a somewhat upright growth habit when young and does not produce basal branches, therefore, plants can become open and develop a "leggy" base. *Prunus* x *cistena* 'UCONNPC001' has a mounded form, with a dense habit and many basal branches, so it remains full at the base of the plant. Flowering is profuse in April, with the production of numerous small (2 cm diameter), single, 5-petaled, light pink to near white, fragrant flowers that attract pollinators. Fruits are scarce due to the hybrid nature of the plant so the plant will not become invasive. If fruits are present they are black-purple and about 1 cm in diameter. Spring and early summer foliage is a vivid reddish purple which becomes more muted as the summer progresses. Leaves in shade may become purplish-dark green. Fall foliage color is typically a purple-red. Propagation is easy by rooting of firm softwood cuttings and by micropropagation. Plants are easy to grow in containers using standard container nursery production practices. Market-ready plants can be produced in 2 to 3 years. Cold hardiness has not been fully evaluated, but the plant should be fully hardy as far north as zone 3. Plants are landscape adaptable and will perform well in most landscape situations that have well-drained soil and light shade to full sun exposure.

BRIEF DESCRIPTION OF THE PHOTOGRAPHS

The accompanying colored photographs illustrate the overall appearance of the new Sand Cherry plant showing the colors as true as it is reasonably possible to obtain in colored reproductions of this type. Colors in the photographs may differ slightly from the color values cited in the detailed botanical description which accurately describe the colors of the new Sand Cherry plant.

The photograph in FIG. 1 is a side perspective view of a mature plant of *Prunus* x *cistena* 'UCONNPC001' grown outdoors in a container nursery at the end of the summer.

Figure 2:
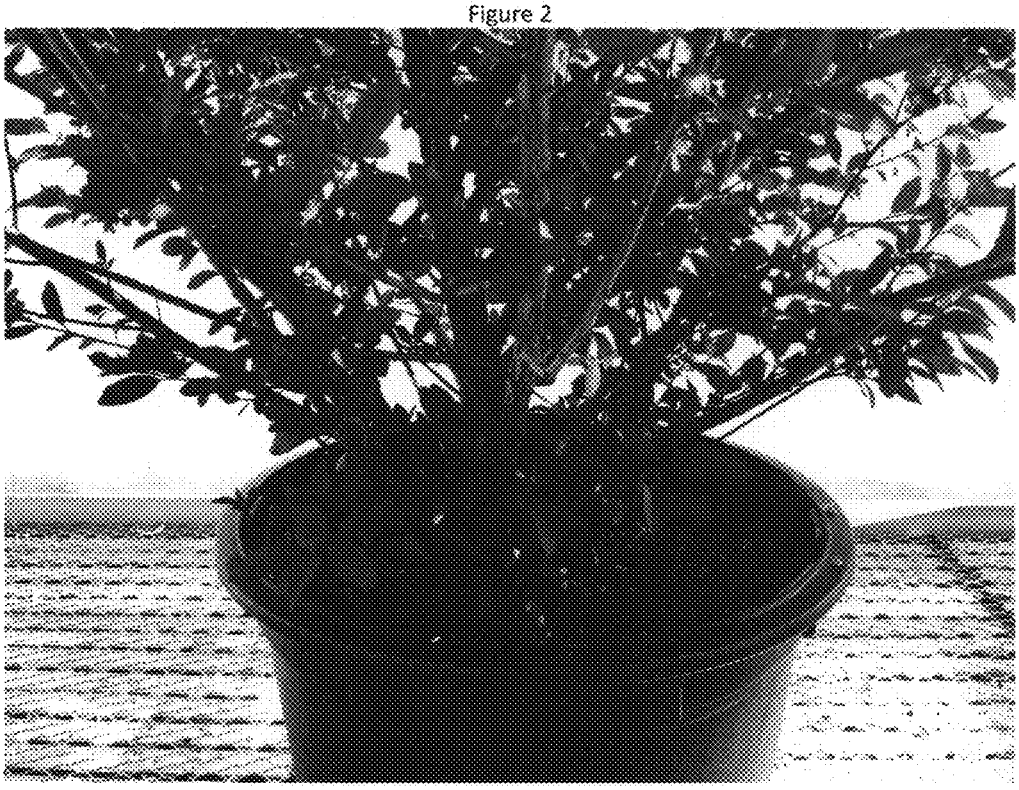

The photograph in FIG. 2 shows the basal branching that is typical of *Prunus* x *cistena* 'UCONNPC001'.

Figure 3:
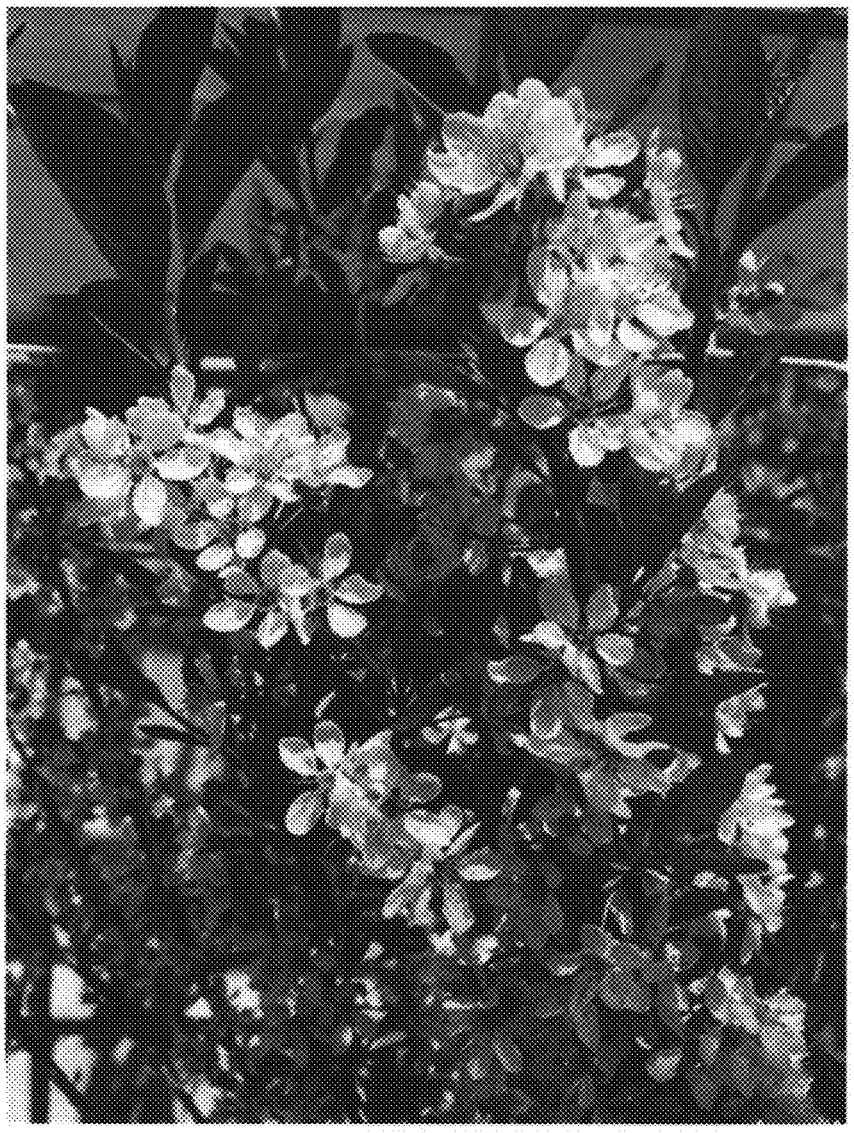

The photograph in FIG. 3 is a close-up view of the typical density of spring flowers along stems produced the previous growing season of *Prunus* x *cistena* 'UCONNPC001'.

Figure 4:
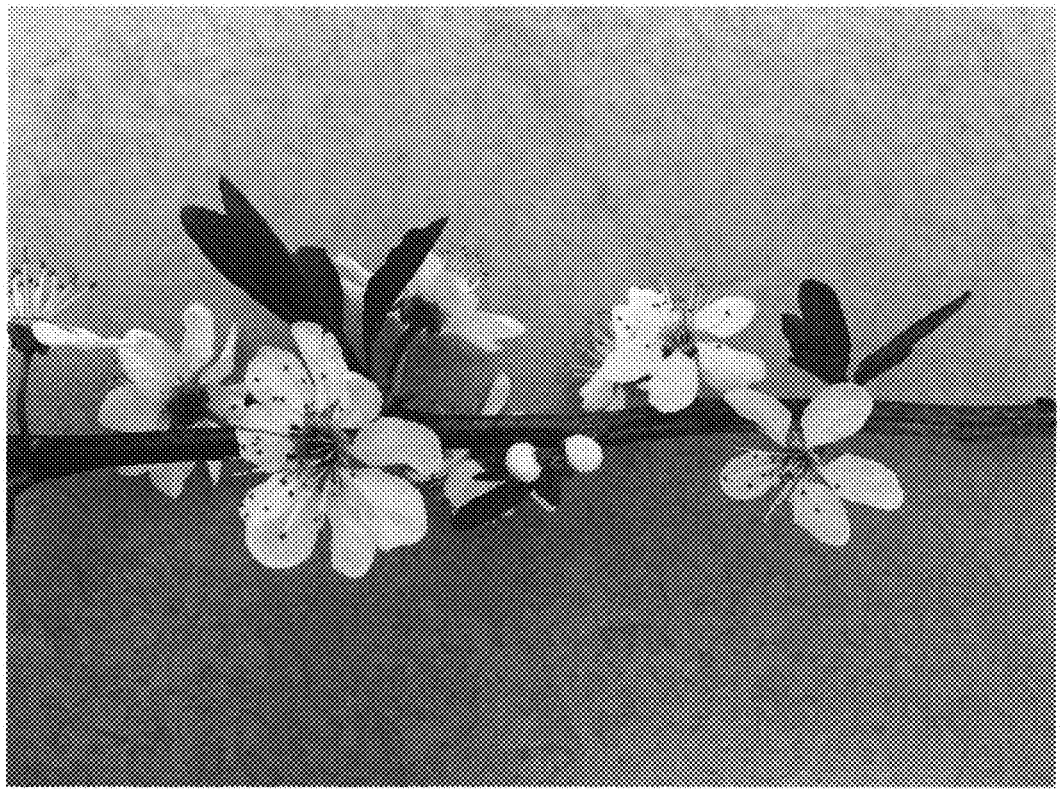

The photograph in FIG. 4 shows 5-petaled flowers and an extra-petaled flower of *Prunus* x *cistena* 'UCONNPC001'.

Figure 5:
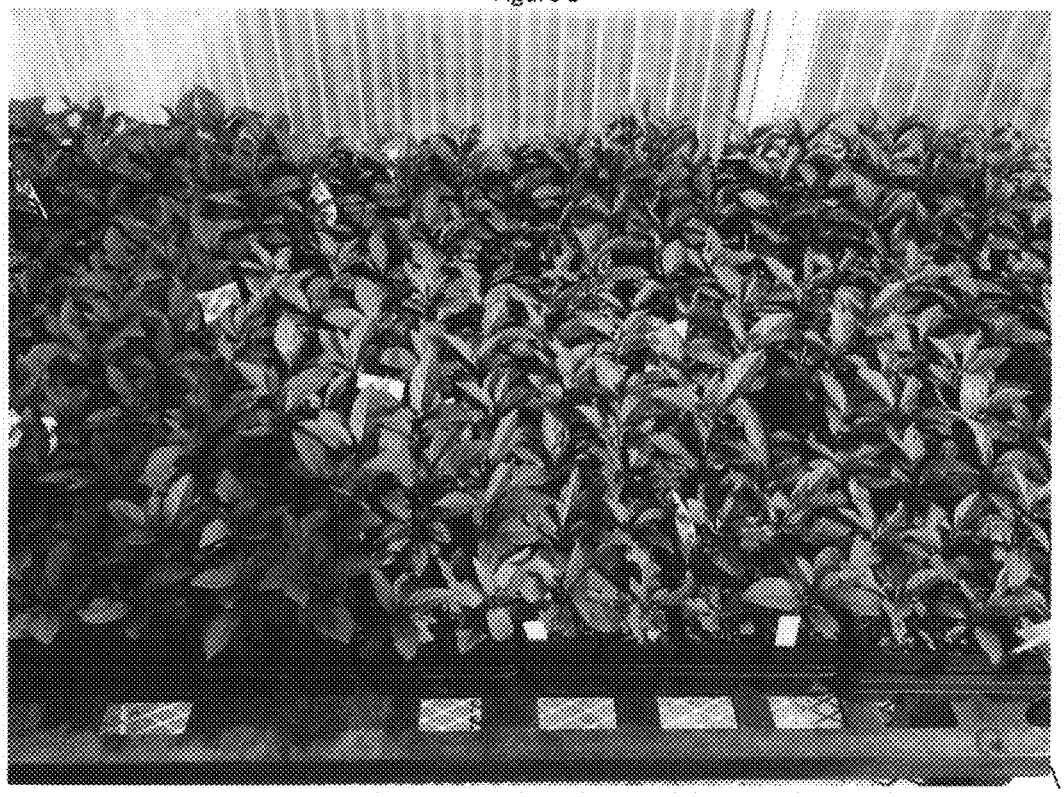

The photograph in FIG. 5 shows young liner plants of *Prunus* x *cistena* 'UCONNPC001' in the greenhouse that were produced via micropropagation in tissue culture.

Figure 6:
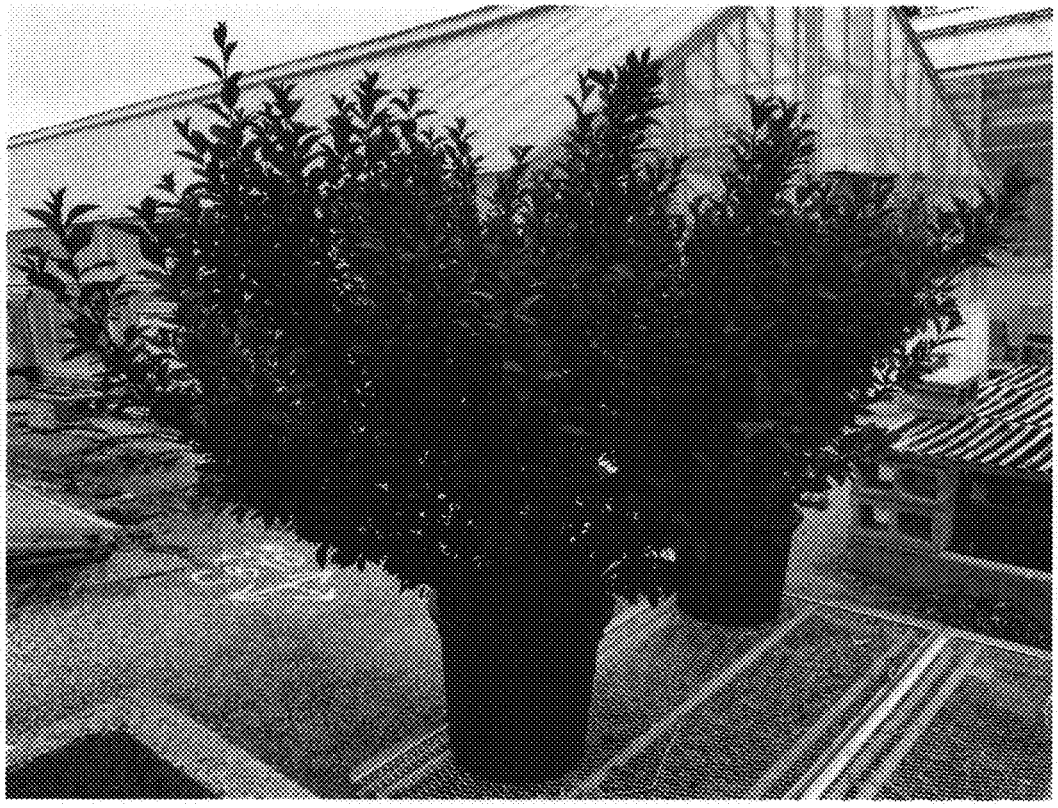

The photograph in FIG. 6 shows a mature *Prunus* x *cistena* 'UCONNPC001' plant with early season foliage color.

Figure 7:
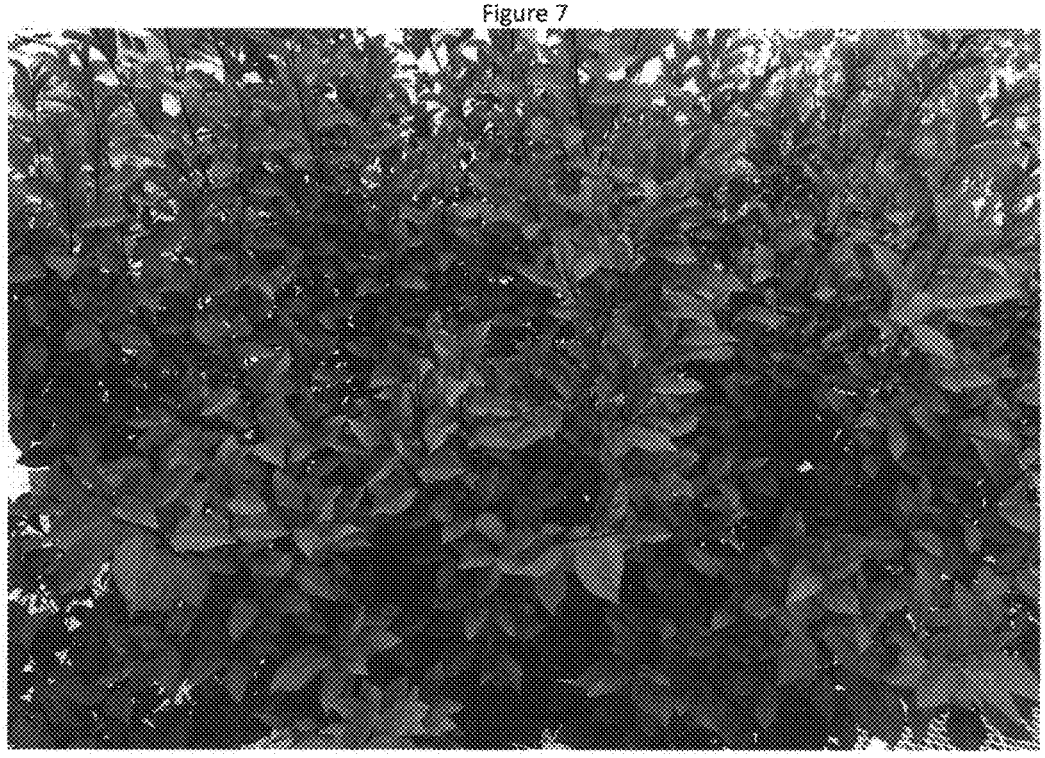

The photograph in FIG. 7 shows a close-up view of the early season foliage color on *Prunus* x *cistena* 'UCONNPC001'.

DETAILED BOTANICAL DESCRIPTION

The aforementioned photographs and following observations, measurements and values describe plants grown during the spring in containers in an outdoor nursery in Storrs, Conn. and under cultural practices which closely approximate commercial Sand Cherry production. The photograph of micropropagated plantlets was of plants in a greenhouse in Storrs, Conn. Plants used for the photographs and description were four years old. In the following detailed description, color references are made to The Royal Horticultural Society Colour Chart, 1995 Edition, except where general terms of ordinary dictionary significance are used.

Botanical classification: *Prunus* x *cistena* 'UCONNPC001'.

Parentage:

*Female, or seed, parent.*—*Prunus pumila* var. *depressa* x *Prunus pumila* var. *susquehanae*, not patented.

*Male, or pollen, parent.*—*Prunus cerasifera* var. *atropurpurea*, not patented.

Propagation:

*Type.*—Softwood cuttings, but must be firm at the base. 1,000 to 3,000 ppm IBA in talc.

*Type.*—Micropropagation using in vitro shoot multiplication followed by microshoot rooting. Murashige and Skoog medium containing 0.5 mg/l benzyladenine for shoot multiplication. Microshoots root easily in humidity chambers under non-sterile conditions with 1,000 ppm indole butyric acid in talc dip.

*Time to initiate roots* (*softwood cutting*), *summer.*—About 1.5 months at temperatures about 80-85 F.

*Time to produce a rooted young plant, summer.*—About 1.5 months at temperatures about 80-85 F.

*Root description.*—Fine, reddish-pink roots.

*Rooting habit.*—Fibrous and profuse.

Plant description:

*Plant form and growth habit.*—Mounded and dense.

*Plant height.*—About 140 cm.

*Plant diameter* (*area of spread*).—About 180 cm.

Lateral branch description:

*Length.*—About 10-50 cm.

*Diameter.*—About 2 mm to 3 mm.

*Internode length.*—About 1-2 cm.

*Aspect.*—45-60 degree angle from stem.

*Strength.*—Firm, but flexible.

*Texture.*—Smooth.

*Color.*—Close to 200A, 200B, 200C and 200D.

*Thorns.*—Quantity: None.

Leaf description:

*Arrangement.*—Alternate.

*Length.*—About 7 cm.

*Width.*—About 3.5 cm.

*Shape.*—Elliptical.

*Apex.*—Broadly acute.

*Base.*—Broadly acute.

*Margin.*—Evenly serrulate.

*Texture, upper and lower surfaces.*—Slightly embossed veins, otherwise glabrous.

*Venation pattern.*—Pinnate.

*Color.*—Developing leaves, upper surface: Close to 60A, 60B, 46A, 185A under high light conditions. Developing leaves, lower surface: Close to 60A, 60B, 46A, 185A under high light conditions. Fully expanded young leaves, upper surface: Close to 187A under high light conditions; venation, close to 187B. Fully expanded young leaves, lower surface: Close to 59A, 187C under high light conditions; venation, close to 59C. Fully expanded old leaves under high light conditions, or younger expanded leaves in shaded interior, upper surface: Close to 139A, 187A; venation, close to 187D. Fully expanded old leaves under high light conditions, or younger expanded leaves in shaded interior, lower surface: Close to 189A, 147A; venation, close to 187D.

*Petiole*.—Length: About 10 mm. Diameter: About 1-2 mm. Texture, upper and lower surfaces: glabrous. Color, upper and lower surfaces: Close to 187A or 187B.

Flower description:

*Flower arrangement and habit*.—Numerous small flowers occur all along the length of the previous season's annual growth; typically 30-40 flowers per 15 cm length of stem, ranging from 20-60 or so flowers. Flowers occur at each node, numbering between 1-8 flowers per node; typically 4 per node.

*Fragrance*.—Significantly fragrant with a sweet, perfumed scent.

*Natural flowering season*.—Late April to early May in Connecticut.

*Flower longevity*.—10-14 days.

*Inflorescence length*.—About 2 cm.

*Inflorescence diameter*.—About 4 cm.

*Flower diameter*.—About 20 mm for 5 petal flowers; about 25 mm for extra petal flowers.

*Flower length* (*height*).—About 10 mm.

*Flower buds*.—Length: About 2-8 mm. Diameter: About 2-5 mm. Shape: Rounded. Color: Close to 69A, 69B, 69C, 69D, 76D, 155C.

*Petals*.—Arrangement: 5 petals in a single whorl; some flowers with a higher number of petals ranging from 6-9. Length: About 9 mm. Width: About 5 mm. Shape: Elliptical. Apex: Rounded. Base: Acute, tapering rapidly to a thin attachment at the receptacle. Margin: Entire, with slight irregular teeth. Texture, Upper and lower surfaces: smooth. Color: When opening, upper and lower surfaces: 69A, 69B, 69C, 69D, 76D, 155C. Fully opened, upper and lower surfaces: same as for opening.

*Sepals*.—Arrangement: 5 sepals in a single whorl, but extra petal flowers have 6-9 sepals. Length: About 2.5 mm. Width: About 2 mm. Shape: Broadly strap-like with rounded tip. Apex: Rounded. Base: Squared. Margin: Ciliate. Texture, Upper and lower surfaces: smooth. Color: Center 146C, margin 61B.

*Pedicels*.—Length: About 10-14 mm. Diameter: About 1 mm. Aspect: About 30 degrees to 60 degrees from stem axis. Strength: firm. Texture: smooth. Color: Close to 146C.

*Reproductive organs*.—Stamens: Quantity: 20-25 on 5-petal flowers; 40-45 on extra-petal flowers. Anther shape: Two kidney halves that together make a rounded form. Anther length: About <1 mm. Anther color: Close to 180B. Pollen amount: Scarce to moderate amount. Pollen color: Close to 163A. Filament color: 75D, 186D, 186C. Filament length: 5-7 mm. Receptacle color at filament attachment point: 186C. Pistils: Quantity: 1 per flower. Pistil length: About 6-7 mm. Style length: About 6-7 mm. Style color: Close to 62D. Stigma color: Close to 62D. Ovary color: Close to 63B. Seeds and fruits: Seed and fruit development have been observed on plants of the new Sand Cherry, but form very infrequently. When present, they are usually solitary, about 1 cm in diameter and are shiny black (closest to 202A and 187A).

Garden performance: Plants of the new Sand Cherry have been observed to have excellent garden performance in full sun and well-drained soils. They tolerate winter minimum temperatures down to about −30 F and are best adapted to locations receiving fewer than 50 summer days with temperatures exceeding 86 F.

Pathogen & pest resistance: Plants of the new Sand Cherry have been observed to be resistant to powdery mildew. Plants of the new Sand Cherry have not been shown to be resistant to pests and other pathogens common to Sand Cherry plants.

It is claimed:

1. A new and distinct Sand Cherry plant named *Prunus* x *cistena* 'UCONNPC001' as illustrated and described.

* * * * *